United States Patent [19]

Bedekovic et al.

[11] Patent Number: 5,166,350
[45] Date of Patent: Nov. 24, 1992

[54] PROCESS FOR THE MANUFACTURE OF FLUORAN COMPOUNDS

[75] Inventors: Davor Bedekovic, Biel-Benken, Switzerland; Jerry L. Pool, Greensboro, N.C.; Brian J. Williams, Stockport, England; Robert Garner, Bury, England; John B. Henshall, Manchester, England

[73] Assignee: Ciba-Geigy Corporation, Ardsley, N.Y.

[21] Appl. No.: 769,741

[22] Filed: Sep. 30, 1991

Related U.S. Application Data

[63] Continuation of Ser. No. 536,815, Jun. 11, 1990, abandoned.

[30] Foreign Application Priority Data

Jun. 10, 1989 [GB] United Kingdom ............... 8913415

[51] Int. Cl.$^5$ ............... C07D 493/10; C07D 211/14
[52] U.S. Cl. ............... 546/15; 549/224; 549/225; 549/226; 548/407
[58] Field of Search ............... 549/225, 224, 226; 546/15; 548/407

[56] References Cited

U.S. PATENT DOCUMENTS

| | | | |
|---|---|---|---|
| 3,681,396 | 8/1972 | Lin | 549/226 |
| 3,746,562 | 7/1973 | Lin | 549/226 |
| 3,873,573 | 3/1975 | Farber et al. | 549/226 |
| 3,920,510 | 11/1975 | Hatano et al. | 549/226 |
| 4,024,157 | 5/1977 | Hotta et al. | 549/226 |
| 4,302,393 | 11/1981 | Garner et al. | 503/302 |
| 4,330,973 | 5/1982 | Hatano et al. | 549/226 |
| 4,364,999 | 12/1982 | Motohashi et al. | 503/221 |
| 4,444,591 | 4/1984 | Kawai et al. | 549/226 |
| 4,510,513 | 4/1985 | Yamaguchi et al. | 503/217 |
| 4,806,675 | 2/1989 | Zink | 549/226 |

FOREIGN PATENT DOCUMENTS

| | | |
|---|---|---|
| 0089752 | 9/1983 | European Pat. Off. |
| 0110366 | 6/1984 | European Pat. Off. |
| 0112710 | 7/1984 | European Pat. Off. |
| 0115821 | 8/1984 | European Pat. Off. |
| 0155593 | 9/1985 | European Pat. Off. |
| 0155796 | 9/1985 | European Pat. Off. |
| 0176161 | 4/1986 | European Pat. Off. |
| 0435149 | 7/1991 | European Pat. Off. |

*Primary Examiner*—Richard L. Raymond
*Assistant Examiner*—Mark W. Russell
*Attorney, Agent, or Firm*—Kevin T. Mansfield; Edward McC. Roberts

[57] ABSTRACT

A process for the preparation of a fluoran compound of the formula

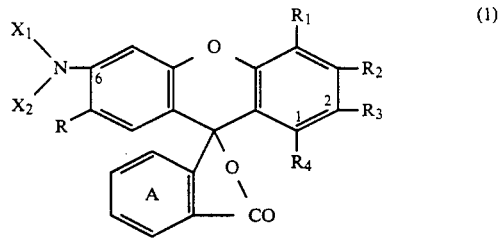

wherein
R, $R_1$, $R_2$ and $R_4$ are each independently hydrogen, halogen, lower alkyl or lower alkoxy,
$R_3$ is hydrogen, halogen, lower alkyl, lower alkoxy or $-NX_3X_4$, or ($R_1$ and $R_2$) or ($R_3$ and $R_4$) each pair together with the carbon atoms to which they are attached, form a fused benzene nucleus,
$X_1$, $X_2$, $X_3$ and $X_4$ are each independently hydrogen, alkyl containing not more than 12 carbon atoms which is unsubstituted or substituted by cyano, halogen, hydroxy, tetrahydrofuryl or lower alkoxy, or are cycloalkyl, aryl or aralkyl or ($X_1$ and $X_2$) or ($X_3$ and $X_4$) are each independently together with the nitrogen to which are attached a 5- or 6-membered heterocyclic ring, and
the ring A is unsubstituted or substituted by halogen, nitro, lower alkyl, lower alkylthio, lower alkoxy, lower alkoxycarbonyl, amino, mono-lower alkylamino, di-lower alkylamino or lower alkyl carbonylamino,
which process comprises
(1) reacting a ketonic acid of the formula

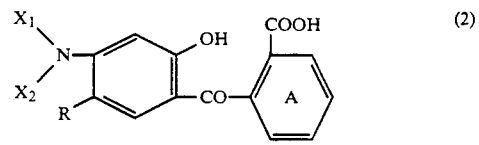

with a substituted phenol derivative of the formula

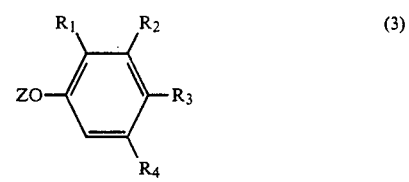

wherein Z is hydrogen, lower alkyl, formyl or lower alkanoyl and A, R, $R_1$, $R_2$, $R_3$, $R_4$, $X_1$ and $X_2$ have the given meanings,
(2) adding the reaction product to an aqueous-organic liquor containing a non-polar organic solvent and a base at a temperature of 50° to 90° C.,
(3) separating the organic phase and
(4) removing the organic solvent to obtain the fluoran of the formula (1).

21 Claims, No Drawings

PROCESS FOR THE MANUFACTURE OF FLUORAN COMPOUNDS

This application is a continuation, of application Ser. No. 536,815, filed Jun. 11, 1990, abandoned.

The present invention relates to a novel process for the manufacture of fluoran compounds, in particular of 2,6-diaminofluorans which contain in the 2-position an amino group which is mono- or disubstituted by an aliphatic, cycloaliphatic or preferably by an araliphatic or aromatic radical.

Surprisingly, it has now been found that the overall process time can be shortened, the preparatory process simplified and the yield and quality of the fluorans improved, by carrying out an acid or alkaline quench at a temperature of 50° to 90° C. after the condensation step and before the formation of the fluoran.

Accordingly, the present invention provides a process for the manufacture of fluoran compounds which have the formula

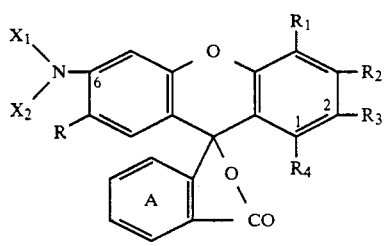

wherein

R, $R_1$, $R_2$ and $R_4$ are each independently hydrogen, halogen, lower alkyl or lower alkoxy, $R_3$ is hydrogen, halogen, lower alkyl, lower alkoxy or $-NX_3X_4$, or ($R_1$ and $R_2$) or ($R_3$ and $R_4$) each pair together with the carbon atoms to which they are attached, form a fused benzene nucleus, $X_1$, $X_2$, $X_3$ and $X_4$ are each independently hydrogen, alkyl containing not more than 12 carbon atoms which is unsubstituted or substituted by cyano, halogen, hydroxy, tetrahydrofuryl or lower alkoxy, or are cycloalkyl, aryl or aralkyl or ($X_1$ and $X_2$) or ($X_3$ and $X_4$) are each independently together with the nitrogen to which they are attached a 5- or 6-membered, preferably saturated, heterocyclic ring, and the ring A is unsubstituted or substituted by halogen, nitro, lower alkyl, lower alkylthio, lower alkoxy, lower alkoxycarbonyl, amino, mono-lower alkylamino, di-lower alkylamino or lower alkyl carbonylamino.

The process comprises (1) reacting a ketonic acid of the formula

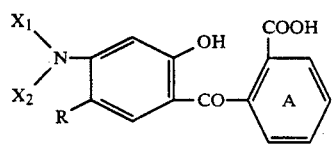

with a substituted phenol derivative of the formula

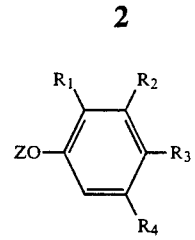

wherein Z is hydrogen, lower alkyl, formyl or lower alkanoyl and A, R, $R_1$, $R_2$, $R_3$, $R_4$, $X_1$ and $X_2$ have the given meanings, (2) adding the reaction product to an aqueous-organic liquor containing a non-polar organic solvent, preferably toluene or xylene, and a base at a temperature of 50° to 90° C. advantageously for 15 to 120 minutes, (3) separating the organic phase and (4) removing the organic solvent to obtain the fluoran of the formula (1).

Z is preferably hydrogen, methyl, ethyl, formyl or acetyl. Most preferably, Z is hydrogen or, in particular, methyl.

In the definition of the radicals of the fluorans, lower alkyl, lower alkoxy and lower alkylthio usually denote those groups or moieties which contain from 1 to 6, preferably from 1 to 4 carbon atoms. Examples of such groups are: methyl, ethyl, n-propyl, isopropyl, n-butyl, sec-butyl, tert-butyl, amyl, isoamyl or hexyl; methoxy, ethoxy, isopropoxy, tert-butoxy or tert-amyloxy; and methylthio, ethylthio, propylthio or butylthio.

Halogen is typically fluorine, bromine, or, preferably, chlorine.

R, $R_1$, $R_2$ and $R_4$ are preferably hydrogen, lower alkyl, especially methyl, lower alkoxy, bromo or chloro.

$R_3$ is preferably halogen, lower alkyl or $-NX_3X_4$.

Alkyl groups $X_1$, $X_2$, $X_3$ and $X_4$ may be in straight-chain or branched-chain configuration and are, for example, methyl, ethyl, n-propyl, isopropyl, n-butyl, sec-butyl, tert-butyl, 1,1,3,3-tetramethylbutyl, amyl, isoamyl, n-hexyl, 2-ethylhexyl, 3,5,5-trimethylhexyl, n-heptyl, n-octyl, isooctyl, n-nonyl, isononyl or n-dodecyl.

Substituted alkyl groups $X_1$, $X_2$, $X_3$ and $X_4$ are preferably cyanoalkyl, haloalkyl, hydroxyalkyl or alkoxyalkyl, each preferably containing in all 2 to 6 carbon atoms. Examples of such groups are: β-cyanoethyl, β-chloroethyl, γ-chloropropyl, β-hydroxyethyl, γ-hydroxypropyl, β-methoxyethyl, β-ethoxyethyl or γ-methoxypropyl, as well as tetrahydrofurfuryl.

$X_1$, $X_2$, $X_3$ and $X_4$ as cycloalkyl are typically cyclopentyl, cycloheptyl or, preferably, cyclohexyl. The cycloalkyl radicals may contain one or more $C_1$–$C_4$alkyl groups, preferably methyl groups, and have in all 5 to 10 carbon atoms.

$X_1$, $X_2$, $X_3$ and $X_4$ as aralkyl may be phenethyl, phenylisopropyl or, preferably, benzyl. Aryl radicals X are preferably naphthyl or, most preferably, phenyl.

Preferred substituents in the aralkyl and aryl moieties of the radicals X are, for example, halogen, cyano, methyl, trifluoromethyl, methoxy or carbomethoxy. Examples of such araliphatic and aromatic radicals are methylbenzyl, 2,4- or 2,5-dimethylbenzyl, chlorobenzyl, dichlorobenzyl, cyanobenzyl, tolyl, xylyl, chlorophenyl, dichlorophenyl, methoxyphenyl, 2,6-dimethylphenyl, trifluoromethylphenyl or carboxymethoxyphenyl.

Heterocyclic radicals —NX$_1$X$_2$ and —NX$_3$X$_4$ are, for example, pyrrolidino, piperidino, pipecolino, morpholino, thiomorpholino or piperazino, for example N-methylpiperazino. Preferred saturated heterocyclic radicals —NX$_1$X$_2$ and —NX$_3$X$_4$ are pyrrolidino, piperidino or morpholino.

The substituents X$_1$ and X$_2$ are preferably cyclohexyl, tolyl, benzyl, cyano-lower alkyl, for example β-cyanoethyl or, preferably, lower alkyl such as methyl, ethyl, n-propyl, isopropyl, n-butyl, isoamyl or n-hexyl. —NX$_1$X$_2$ is preferably also pyrrolidinyl or N—C$_1$-C$_5$-alkyl-N-tetrahydrofurfurylamino such as N-ethyl-N-tetrahydrofurfurylamino.

The substituents X$_3$ and X$_4$ are preferably hydrogen, C$_1$-C$_8$alkyl, cyclohexyl, phenyl, benzyl, or phenyl or benzyl, each substituted by halogen, lower alkyl, especially methyl, methoxy, carbomethoxy or trifluoromethyl.

The ring A is preferably not further substituted. If it does contain substituents, then these are in particular halogen, lower alkoxycarbonyl or di-lower alkylamino. The ring A is preferably unsubstituted or substituted by halogen.

The reactants of formulae (2) and (3) are preferably employed in molar amounts when carrying out the process of this invention.

The process of the present invention for preparing fluorans of the formula (1) is conveniently carried out in four steps in which the intermediates obtained can be further used without isolation.

The first step, in which the ketonic acid of the formula (2) is reacted with the substituted phenol derivative of the formula (3), is suitably carried out in concentrated or fuming sulfuric acid or mixtures thereof, advantageously in the temperature range from 0° to 120° C., preferably from 0° to 65° C. and most preferably from 5° to 45° C. The reaction time of the condensing step depends usually on the temperature and on the starting materials and is generally from ½ hour to 10 hours, preferably from 1 to 5 hours. The condensing temperature may be of 25° to 40° C. for 2-3 hours and subsequently of 45° to 65° C. for 2-4 hours. Concentrated sulphuric acid has a concentration of e.g. 50-100%, preferably 90-98%. The SO$_3$ content of the fuming sulphuric acid is preferably 20-22 weight percent. Upon the completion of the first step, the reaction product is quenched direct into an aqueous-organic medium at a temperature of 50° to 90° C., preferably 75° to 85° C. This second step is preferably carried out by either adding the sulfuric acid containing solution obtained in the first step to said medium containing a base, or first to said medium containing diluted sulfuric acid and then adding the base.

The reaction time of the second step is generally from 15 to 120 minutes, preferably from 25 to 60 minutes.

The organic part of the medium consists of an appropriate non-polar solvent e.g. benzene, monochlorobenzene, dichlorobenzene, trichlorobenzene, nitrobenzene or preferably toluene or xylene.

Suitable bases are alkali metal hydroxides, e.g. sodium or potassium hydroxide, ammonia, alkali metal carbonates or bicarbonates, ammonium carbonate or ammonium bicarbonate, dialkyl- or trialkylamines or dialkanol- or trialkanolamines; and mixtures thereof. The most preferred base is sodium hydroxide.

To obtain the desired final product the organic phase, which results after the quench and ring closure (cyclization), is separated and the organic solvent is removed, e.g. by steam distillation whereupon the final product of formula (1) precipitates.

Thus the final product is isolated in a generally known manner by separating the precipitate and washing and drying the filter cake, or by treating it with a suitable organic solvent, e.g. methanol, ethanol or isopropanol, and if necessary, recrystallising the product e.g. from toluene.

A particularly suitable embodiment of the novel process comprises condensing the ketonic acid of the formula (2) and the phenol derivative of the formula (3) in a mixture of concentrated and fuming sulfuric acid in the temperature range from 10° to 40° C., preferably for 1 to 3 hours, quenching the obtained reaction mass (a) into an aqueous-organic medium containing toluene or xylene and a base, e.g. sodium or potassium hydroxide and having a temperature of 70° to 85° C., or (b) into an aqueous-organic medium containing toluene or xylene and then adding a base, e.g. sodium hydroxide, at 60° to 90° C., preferably 70° to 85° C., and finally separating the toluene or xylene phase and isolating the fluoran of the formula (1) by removing the solvent.

Examples of ketonic acids of the formula (2) employed as starting materials are:
2-(4'-dimethylamino-2'-hydroxybenzoyl)benzoic acid,
2-(4'-diethylamino-2'-hydroxybenzoyl)benzoic acid,
2-(4'-di-n-butylamino-2'-hydroxybenzoyl)benzoic acid,
2-(4'-di-n-pentylamino-2'-hydroxybenzoyl)benzoic acid,
2-(4'-N-methyl-N-cyclohexylamino-2'-hydroxybenzoyl)benzoic acid,
2-(4'-N-phenyl-N-methylamino-2'-hydroxybenzoyl)-benzoic acid,
2-(4'-N-o-, m- or p-toyl-N-methylamino-2'-hydroxybenzoyl)benzoic acid,
2-(4'-N-o-, m- or p-tolyl-N-ethylamino-2'-hydroxybenzoyl)benzoic acid,
2-(4'-N-pyrrolidino-2'-hydroxybenzoyl)benzoic acid,
2-(4'-N-piperidino-2'-hydroxybenzoyl)benzoic acid,
2-(4'-N-methyl-N-n-amylamino-2'-hydroxybenzoyl)-benzoic acid,
2-(4'-N-ethyl-N-isoamylamino-2'-hydroxybenzoyl)benzoic acid,
2-(4'-dibenzylamino-2'-hydroxybenzoyl)benzoic acid,
2-(4'-dimethylamino-5'-methyl-2'-hydroxybenzoyl)benzoic acid,
2-(4'-diethylamino-5'-methyl-2'-hydroxybenzoyl)benzoic acid,
2-(4'-dimethylamino-5'-methyl-2'-hydroxybenzoyl)-3,4,5,6-tetrachlorobenzoic acid,
2-(4'-di-β-ethoxyethylamino-2'-hydroxybenzoyl)benzoic acid,
2-(4'-di-β-cyanoethylamino-2'-hydroxybenzoyl)benzoic acid,
2-(4'-(N-tetrahydrofurfuryl-N-ethylamino)-2'-hydroxybenzoyl)benzoic acid,
2-(4'-(N-methyl-N-n-propylamino)-2'-hydroxybenzoyl)benzoic acid,
2-(4'-(N-methyl-N-isopropylamino)-2'-hydroxybenzoyl)benzoic acid,
2-(4'-(N-ethyl-N-n-hexylamino)-2'-hydroxybenzoyl)-benzoic acid,
2-(4'-dimethylamino-5'-methyl-2'-hydroxybenzoyl)4,5-dichloro-benzoic acid,
2-(4'-phenylamino-2'-hydroxybenzoyl)-benzoic acid,
2-(4'-diethylamino-2'-hydroxybenzoyl)-3,4,5,6-tetrachloro-benzoic acid, 2-(4'-diethylamino-2'-hydroxybenzoyl)-4/5-tert-butyl-benzoic acid.

Representative examples of substituted phenol derivatives of formula (3) are:
4-ethylaminophenol, 4-n-octylaminophenol, 4-tert-butylphenol,
4-n-octylamino-1-methoxybenzene,
4-dibenzylamino-1-methoxybenzene,
4-(4'-chlorophenylamino)-1-methoxybenzene,
4-(2'-chlorophenylamino)-1-methoxybenzene,
4-(3'-trifluorophenylamino)-1-methoxybenzene,
4-phenylamino-3-methyl-1-methoxybenzene,
4-N-methyl-N-phenylamino-1-methoxybenzene,
4-(2',4'-dimethylanilino)-1-methoxy-3-methylbenzene,
4-(3',4'-dichloroanilino)-1-methoxybenzene,
4-dibenzylamino-3-methyl-1-methoxybenzene,
4-dibenzylamino-2-methyl-1-methoxybenzene,
4-phenethylamino-1-methoxybenzene,
4-cyclohexylamino-1-methoxybenzene,
4-xylylamino-1-methoxybenzene,
4-p-toluidino-1-methoxybenzene,4-(4'-n-butylphenylamino)-1-methoxybenzene,
2,4-dimethyl-1-methoxybenzene,
3-chloro-4-methyl-1-methoxybenzene,
4-tert-butyl-1-methoxybenzene,
2-methoxy-naphthalene,3-methyl-4-chloro-1-methoxybenzene,
3-chloro-1-methoxybenzene,4-chloro-1-methoxybenzene.

The preferred fluoran compounds which are prepared by the process of this invention are those which are substituted by basic groups and are of the formula (1), wherein each of R, $R_1$, $R_2$ and $R_4$ independently is hydrogen, chlorine or methyl, each of $X_1$ and $X_2$ independently is $C_1$–$C_8$alkyl, cyclohexyl, tolyl or benzyl or —$NX_1X_2$ is pyrrolidino or piperidino, $R_3$ is —$NX_3X_4$, $X_3$ is $C_1$–$C_8$alkyl, phenyl, chlorophenyl, trifluoromethylphenyl, tolyl, xylyl or benzyl, $X_4$ is hydrogen, lower alkyl or benzyl and the ring A is unsubstituted. The most preferred fluoran compounds of the formula (1) are those wherein R, $R_1$ and $R_4$ are hydrogen, $R_2$ is hydrogen or methyl, and each of $X_1$ and $X_2$ is lower alkyl or cyclohexyl, or —$NX_1X_2$ is pyrrolidino, $R_3$ is —$NX_3X_4$, $X_3$ is phenyl, tolyl, chlorophenyl, xylyl, trifluoromethylphenyl or benzyl and $X_4$ is hydrogen, methyl or benzyl.

A considerable advantage of the present invention resides in the feature that it is easy to carry out technically and affords pure final products in very good yield without isolation of the phthalide compound obtained as intermediate.

A further advantage of the present invention lies in the fact that at least a five-fold reduction in the quantity of organic waste in the effluent is attained. Depending upon the quenching step used, it is further possible to attain a reduction in the amount of inorganic salts contained in the effluent by up to 90%.

The fluoran compounds of the formula (1) prepared by the process of this invention are normally colourless or at most faintly coloured. They are particularly suitable rapidly developing colour formers for use in a heat-sensitive or in a pressure-sensitive recording material which can also be a copying material. When these colour formers are brought into contact preferably with an acid developer, i.e. an electron acceptor, they produce on clays and phenolic substrates strong orange, red, violet, green, grey or black colorations which are fast to sublimation and light.

The invention is illustrated by the following Examples in which percentages are by weight, unless otherwise stated.

EXAMPLE 1

123.7 g of sulphuric acid (98%) and 76.3 g of oleum 22% are charged to a reaction flask fitted with stirrer and thermometer. The temperature rises to 40° C. and is cooled to 25° C. 47.9 g of 4-diethylamino-2-hydroxybenzophenone-2'-carboxylic acid are added, ensuring the temperature does not exceed 30° C. Then 53.3 g of N,N-dibenzyl-4-anisidine are added. The temperature is allowed to rise to 30°–35° C. and kept for 2 hours. After this period the reaction mass is heated over 1 hour to 60° C. and maintained for 3 hours. Afterwards the reaction mass from the condensation step is added over 1 hour to a mixture of 222 ml water, 263 ml of sodium hydroxide solution and 200 ml of toluene and the temperature is maintained at 80°–85° C. After the phase separation the organic layer is washed with hot water and the solvent removed by steam distillation, whereupon the product precipitates.

The product is isolated by filtration, washed with methanol and dried, affording 71 g of the compound of the formula

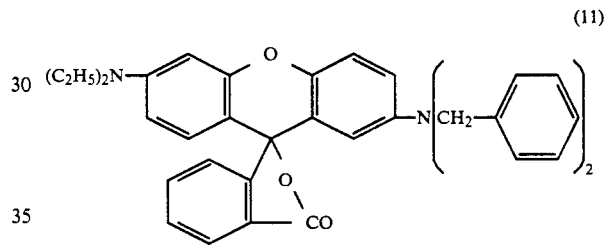

(11)

with a melting point of 173°–174° C.

The yield is 82% of theory, based on 4-diethylamino-2-hydroxybenzophenone-2'-carboxylic acid.

EXAMPLE 2

110 g of sulphuric acid (98%) and 90% are charged to a reaction flask fitted with stirrer and thermometer. The temperature rises to 40° C. It is cooled to 20°–22° C. 47.9 g of 4-diethylamino-2-hydroxybenzophenone-2'-carboxylic acid are added, ensuring the temperature does not exceed 30° C. The mass is stirred until complete solution is obtained and then 53.3 g of N,N-dibenzyl-4-methoxy-aniline are added, again ensuring the temperature does not exceed 30° C., whereupon this temperature is maintained for 2 hours. Afterwards the temperature is raised over 1 hour to 60°–62° C. The reaction mass is kept at this temperature for 3 hours and then cooled to 30°–40° C. After the condensation step ¼ of the reaction mass is added over a period of 1 hour to a mixture having a temperature of 70° C. of 50 ml of hot water and 50 ml of toluene. Afterwards 138.7 ml of cold water and the remaining ¾ of the reaction mass are added simultaneously. 21.3 g of sodium hydroxide solution are added over 15 minutes whilst maintaining a temperature of 80°–85° C. and then the mass is stirred for 20 minutes and allowed to settle for 1 hour.

After the phase separation a mixture of 9.0 g sodium hydroxide solution and 6 g water is added to the toluene solution over 15 minutes and at 80°–85° C. and the mixture having a pH value of 10-11 is stirred 30 minutes at 80°–85° C.

The toluene phase is again separated, washed with hot water and the solvent is distilled off. The product precipitates as a crystalline suspension and is isolated by filtration, washed with methanol and dried. Yield: 72.0 g of 2-dibenzylamino-6-diethylaminofluoran having a melting point of 173°-174° C.

EXAMPLE 3

151.1 g of sulphuric acid (98%) and 48.9 g oleum 22% are charged to a reaction flask fitted with stirrer and thermometer. The temperature rises to 40° C. It is cooled to 25° C. 47.9 g of 4-diethylamino-2-hydroxy-benzophenone-2'-carboxylic acid are added over 1 hour while maintaining a temperature of 30° C. The mass is stirred until complete dissolution is obtained and cooled to 25° C. 39.9 g of 2-methyl-4-methoxy-2',4'-dimethyl-diphenylamine are added while maintaining the temperature at <30° C. The reaction mass is kept at this temperature for 2½ hours.

Afterwards the mass is added under stirring over 60 minutes to a mixture having a temperature of 80° C. of 448 ml of water, 138.6 g of toluene and 400 g of sodium hydroxide solution (47%) and the temperature is maintained at 80°-85° C. for 30 minutes and then the mass is allowed to settle for additional 30 minutes. After the phase separation the toluene layer is washed with water and then again separated, whereupon the solvent is removed by vacuum distillation. During the solvent distillation a crystallized product precipitates. The product is filtered off, washed with methanol and dried.

65.5 g of the compound of the formula

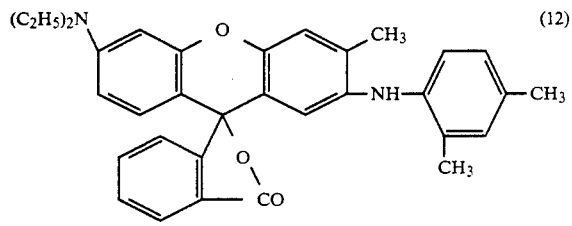

are obtained with a melting point of 171° C. The yield is 85% of theory.

EXAMPLE 4

151.1 g of sulphuric acid (98%) and 48.9 g of oleum (22%) are charged to a reaction flask fitted with stirrer and thermometer. The temperature rises to 40° C. 47.9 g of 4-diethylamino-2-hydroxy-benzophenone-2'-carboxylic acid are added over 1 hour while maintaining a temperature of <30° C. Then 36.9 g of 2-methyl-4-methoxy-2',4'-dimethyldiphenylamine are added keeping the temperature below 30° C. The reaction mass is held with agitation for additional 2½ hours. After the condensation step the reaction mass is added over 1 hour at 75°-80° C. to a mixture 69.8 g of sulphuric acid (50%) and 34.8 g of toluene. Afterwards 156 g of sodium hydroxide solution (10%) are added. The mass is cooled with agitation to 65° C. and allowed to settle for 1 hour.

After the phase separation 104.4 g of toluene and 200 g of sodium hydroxide solution (30%) are added at 75°-80° C. to the organic layer. The mass is stirred for 15 minutes with addition of 50 g of water and is allowed to settle for 60 minutes at 75°-80° C.

The toluene phase is separated for the second time, adjusted to a pH of 10,5-11,5 with 8 g of sodium hydroxide solution (30%), heated to 80°-85° C., stirred 30 minutes at 80°-85° C. and allowed to settle for 15 minutes.

The toluene phase is separated for the third time and the toluene is distilled off, whereupon the crystallized product precipitates. This is filtered off, washed with methanol and dried. Yield: 64 g of the fluoran compound of formula (12), (82,5% of theory).

EXAMPLE 5

160 g of sulphuric acid (81%) are charged to a reaction flask fitted with stirrer and thermometer. The temperature, externally, is adjusted to 70° C. 62.6 g of 4-diethylamino-2-hydroxybenzophenone-2'-carboxylic acid are added over a period of 1 hour, ensuring that the temperature, externally, remains to 70° C. At this temperature 46.8 g of 4-tert-butylphenol are added over 15 minutes and the temperature, externally of 70° C. is maintained for 2 hours. The temperature is raised over 1 hour to 120° C. and is maintained for a further 3 hours. Afterwards the reaction mass is cooled to 40° C. and added over 1 hour, under stirring, to a mixture of 200 g of hot water and 38.2 g of toluene having a temperature of 80° C. The temperature is maintained at 80°-85° C. for 30 minutes. Afterwards the mass is allowed to settle and the organic layer is separated.

The organic layer is added over 1 hour to a mixture of 114.5 g of toluene, 100 g of hot water and 35,5 g sodium hydroxide solution (47%) at a temperature of 80°-85° C. The neutralisation mass is stirred for a further 30 minutes and then is allowed to settle for 30 minutes. After the second phase separation the organic layer is washed with hot water and the solvent is removed by azeotropic distillation at 250 mm Hg and 60°-65° C. The crystallised product obtained is washed with methanol and dried, affording 72 g of the compound of the formula

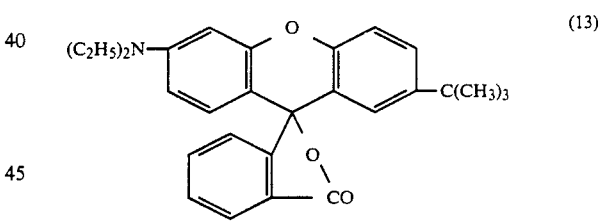

with a melting point of 174°-175.5° C. the yield is 84.4% of theory.

EXAMPLE 6

275.8 g of sulphuric acid (98%) and 88.2 g of oleum 22% are charged to a reaction flask fitted with stirrer and thermometer. The temperature rises to 34° C. and is cooled to 25° C. 77.3 g of 4-diethylamino-2-hydroxybenzophenone-2'-carboxylic acid are added, ensuring the temperature does not exceed 30° C. Then 64.0 g of N-n-octyl-4-anisidine are added and the mass is maintained for 2 hours at 30° C. After this period the reaction mass is heated over 1 hour to 50° C. and maintained for 90 minutes. Afterwards the reaction mass from the condensation step is added over 1 hour to a mixture of 525 ml water, 260 ml of sodium hydroxide solution and 200 ml of toluene at 70° C. and the temperature is raised to 80°-85° C. The reaction mass is stirred for 30 minutes at 80°-85° C. and allowed to settle. After the phase separation the organic layer is washed with hot water and the solvent removed by vacuum distillation at 150 mmHg where upon the product precipitates.

The product is isolated by filtration, washed with methanol and dried, affording 102 g of the compound of the formula

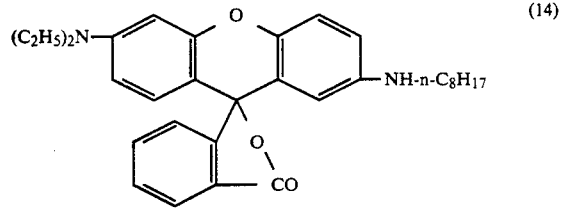

(14)

having a melting point of 126° C. The yield is 83% of theory.

EXAMPLE 7

275.8 g of sulphuric acid (98%) and 88.2 g of oleum (22%) are charged to a reaction flask fitted with stirrer and thermometer. The temperature rises to 34° C. and is cooled to <30° C. 77.3 g of 4-diethylamino-2-hydroxybenzophenone-2'-carboxylic acid are added with stirring, ensuring the temperature does not exceed 30° C. Then 64.0 g of N-n-octyl-4-anisidine are added and the mass is maintained for 2 hours at 30° C. After this period the reaction mass is heated over 1 hour to 50° C. and maintained for 90 minutes. Afterwards the reaction mass from the condensation step is treated with 400 g of water allowing the temperature to raise to 75°–80° C. The diluted reaction mass is added to 140 g of toluene and 102 g of water. Subsequently 196 g of sodium hydroxide solution (47%) are added at a temperature of 75°–80° C. The neutralisation mass is stirred for 30 minutes at 80°–85° C. and settled for 15 minutes. After the phase separation the organic layer is washed with hot water and the solvent is removed by vacuum distillation at 250 mm Hg whereupon the product precipitates.

The product is isolated by filtration, washed with methanol and dried, 103.5 g of 2-n-octylamino-6-diethylaminofluoran having a melting point of 126° C. are obtained.

EXAMPLE 8

151.2 g of sulphuric acid (98%) and 48.8 g of oleum (22%) are charged to a reaction flask fitted with stirrer and thermometer. The temperature rises to 34° C. 47.9 g of 4-diethylamino-2-hydroxy-benzophenone-2'-carboxylic acid are added over 1 hour while maintaining a temperature of <30° C. Then 32.6 g of 2-methyl-4-methoxy-diphenylamine are added keeping the temperature below 30° C. The reaction mass is held with agitation for additional 2½ hours. After the condensation step the reaction mass is treated with 120 g of water and 21.7 g of toluene. Afterwards a sodium hydroxide solution (30%) is added in two portions of 66.0 g and 60 g, respectively. The mass is maintained with agitation at 70° C. and allowed to settle for 1 hour after addition of each portion of the sodium hydroxide solution.

The toluene phase is separated after each addition of the sodium hydroxide solution. The toluene is finally distilled off, whereupon the crystallized product precipitates and is filtered off, washed with methanol and dried.

Yield: 63.5 g of the fluoran compound of the formula

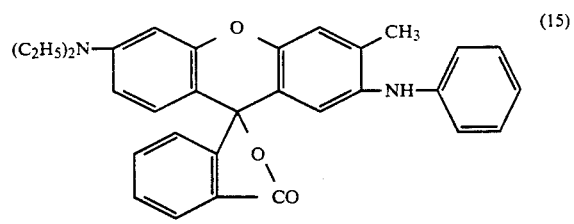

(15)

with a melting point of 193°–195° C. The yield is 87% of theory.

EXAMPLE 9

151.2 g of sulphuric acid (98%) and 48.8 g oleum (22%) are charged to a reaction flask fitted with stirrer and thermometer. The temperature rises to 34° C. It is cooled to 25° C. 47.9 g of 4-diethylamino-2-hydroxybenzophenone-2'-carboxylic acid are added over 1 hour while maintaining a temperature of 30° C. The mass is stirred until complete dissolution is obtained and cooled to 25° C. 32.6 g of 2-methyl-4-methoxydiphenylamine are added while maintaining the temperature at <30° C. The reaction mass is kept at this temperature for 4 hours.

Afterwards the mass is added under stirring over 60 minutes to a mixture having a temperature of 80° C. of 300 ml of water, 195.5 g of toluene and 125.9 g of sodium hydroxide solution (47%) and the temperature is maintained at 80°–85° C. for 2 hours and then the mass is allowed to settle for additional 30 minutes. After the phase separation the toluene layer is washed with water and then again separated, whereupon the solvent is removed by vacuum distillation. During the solvent distillation a crystallised product precipitates. The product is filtered off, washed with methanol and dried. Yield: 66.0 g of 2-phenylamino-3-methyl-6-diethylaminofluoran having a melting point of 193°–195° C. The yield is 91% of theory.

EXAMPLE 10

90 g of sulphuric acid (78%) are charged to a reaction flask fitted with stirrer and thermometer. The temperature is adjusted to 30° C. Afterwards 31.3 g of 4-diethylamino-2-hydroxybenzophenone-2'-carboxylic acid are added over a period of 1 hour, ensuring that the temperature does not exceed 30° C. during the addition. Then, 18.8 g of 4-tert.butylphenol are added over 15 minutes. The temperature is firstly adjusted to 50° C. and maintained for 3 hours and then raised over 1 hour to 120° C. and maintained for a further 3 hours. The reaction mass is cooled to 30° C. and added over 60 minutes under stirring to a mixture of 327 ml water, 200 ml toluene and 160 g of sodium hydroxide solution (47%) having a temperature of 80°–85° C. The temperature is maintained for 1 hour at 80°–85° C. Afterwards the mass is allowed to settle and the organic layer is separated. This latter is washed with hot water and the solvent is removed by steam distillation. After filtration and washing with methanol and drying 36 g of 2-tert.butyl-6-diethylaminofluoran are obtained with a melting point of 174°–175° C.

EXAMPLE 11

200 g of sulphuric acid monohydrate are charged to a reaction flask fitted with stirrer and thermometer. 56.6 g of 4-di-n-butylamino-2-hydroxybenzophenone-2'-carboxylic acid are added over 1 hour while maintaining a temperature of 25°–30° C. Then 32.6 g of 2-methyl-4-methoxy-diphenylamine are added keeping the temperature below 30° C. The reaction mass is held with agitation for 4 hours. After condensation step the reaction mass is treated with 620 g of water, 250 ml of toluene and 270 ml of a sodium hydroxide solution (50%) at 80° C. and allowed to settle for 1 hour after addition of 180 ml of a sulphuric acid solution during 30 minutes. The toluene phase is separated and the toluene is distilled off. The crystallized product precipitates and is filtered off, washed with methanol and dried.

Yield: 70.8 g of the fluoran compound of the formula (16)

with a melting point of 180°–182° C. The yield is 87% of theory.

EXAMPLE 12

200 g sulphuric acid monohydrate are charged to a reaction flask fitted with stirrer and thermometer. 56.6 g of 4-di-n-butylamino-2-hydroxybenzophenone-2'-carboxylic acid are added over 1 hour while maintaining a temperature of 25°–30° C. Afterwards the mass is stirred for 15 minutes at 25°–30° C. Then 35.4 g of 2-methyl-4-methoxydiphenylamine are added and the mass is maintained for 4 hours at 25°–30° C. After the condensation step the reaction mass is added under stirring over 1 hour to a mixture having a temperature of 80° C. of 300 ml of water and 250 ml of toluene. Afterwards 400 ml of water and 60 ml of sodium hydroxide solution (50%) are added. The mass is maintained with agitation at 70° C. and allowed to settle for 10 minutes. The toluene phase is separated and the toluene is distilled off. The crystallized product precipitates and is filtered off, washed with methanol and dried.

Yield: 71.3 g of 2-phenylamino-3-methyl-6-di-n-butylaminofluoran with a melting point of 180°–182° C. The yield is 87.6% of theory.

What is claimed is:

1. A process for the preparation of a fluoran compound of the formula (1)

wherein R, $R_1$, $R_2$ and $R_4$ are each independently hydrogen, halogen, lower alkyl or lower alkoxy, $R_3$ is hydrogen, halogen, lower alkyl, lower alkoxy or —$NX_3X_4$, or ($R_1$ and $R_2$) or ($R_3$ and $R_4$), each pair together with the carbon atoms to which they are attached, form a fused benzene nucleus, $X_1$, $X_2$, $X_3$ and $X_4$ are each independently hydrogen, alkyl containing not more than 12 carbon atoms which is unsubstituted or substituted by cyano, halogen, hydroxy, tetrahydrofuryl or lower alkoxy, or are cycloalkyl, aryl or aralkyl or ($X_1$ and $X_2$) or ($X_3$ and $X_4$) are each independently together with the nitrogen to which they are attached a 5- or 6-membered heterocyclic ring, and the ring A is unsubstituted by halogen, nitro, lower alkyl, lower alkylthio, lower alkoxy, lower alkoxycarbonyl, amino, mono-lower alkylamino, di-lower alkylamino or lower alkyl carbonylamino, which process comprises (1) reacting a ketonic acid of the formula (2)

with a substituted phenol derivative of the formula (3)

wherein Z is hydrogen, lower alkyl, formyl or lower alkanoyl and A, R, $R_1$, $R_2$, $R_3$, $R_4$, $X_1$ and $X_2$ have the given meanings, in concentrated or fuming sulfuric acid or in a mixture thereof at 0° to 120° C., (2) adding the reaction product to an aqueous liquor containing a non-polar organic solvent and a base at a temperature of 50° to 90° C., (3) separating the organic phase and (4) removing the organic solvent to obtain the fluoran of the formula (1).

2. A process according to claim 1, wherein Z is hydrogen, methyl, ethyl, formyl or acetyl.

3. A process according to claim 1, wherein Z is hydrogen or methyl.

4. A process according to claim 1, wherein each of R, $R_1$, $R_2$ and $R_4$ independently is hydrogen, methyl, lower alkoxy, bromo or chloro.

5. A process according to claim 1, wherein $R_3$ is halogen, lower alkyl or —$NX_3X_4$.

6. A process according to claim 1, wherein $X_1$ and $X_2$ are lower alkyl, cyano-lower alkyl, cyclohexyl, phenyl, tolyl or benzyl, or —$NX_1X_2$ is pyrrolidino or N—C$_1$–C$_5$-alkyl-N-tetrahydrofurfurylamino.

7. A process according to claim 1, wherein $X_3$ and $X_4$ are hydrogen, $C_1$–$C_8$-alkyl, cyclohexyl, phenyl, benzyl, or phenyl or benzyl each substituted by halogen, methyl, methoxy, carbomethoxy or trifluoromethyl.

8. A process according to claim 1, wherein the ring A is unsubstituted or substituted by halogen.

9. A process according to claim 1, wherein each of R, $R_1$, $R_2$ and $R_4$ independently is hydrogen, chlorine or methyl, each of $X_1$ and $X_2$ independently is $C_1$–$C_8$-alkyl, cyclohexyl, tolyl or benzyl, or —NX$_1$X$_2$ is pyrrolidino or piperidino, R$_3$ is —NX$_3$X$_4$, X$_3$ is C$_1$-C$_8$-alkyl, phenyl, chlorophenyl, trifluoromethylphenyl, tolyl, xylyl or benzyl, X$_4$ is hydrogen, lower alkyl or benzyl and the ring A is unsubstituted.

10. A process according to claim 1, wherein R, R$_1$ and R$_4$ are hydrogen, R$_2$ is hydrogen or methyl, R$_3$ is —NX$_3$X$_4$, each X$_1$ and X$_2$ is lower alkyl or cyclohexyl, or —NX$_1$X$_2$ is pyrrolidino, X$_3$ is phenyl, tolyl, xylyl, chlorophenyl, trifluoromethylphenyl or benzyl and X$_4$ is hydrogen, methyl or benzyl.

11. A process according to claim 1, wherein the reactant of formula (2) is 2-(4'-diethylamino-2'-hydroxybenzoyl)benzoic acid or 2-(4'-di-n-butylamino-2'-hydroxybenzoyl)-benzoic acid.

12. A process according to claim 1, wherein the reactant of formula (3) is 4-phenylamino-3-methyl-1-methoxybenzene, 4-(2',4'-dimethylphenylamino)-3-methyl-1-methoxybenzene, 4-n-octylamino-1-methoxybenzene, 4-dibenzylamino-1-methoxybenzene or 4-tert.butylphenol.

13. A process according to claim 1, wherein the reactants of formulae (2) and (3) are 2-(4'-diethylamino-2'-hydroxybenzoyl)benzoic acid and 4-phenylamino-3-methyl-1-methoxybenzene, 4-(2',4'-dimethylphenylamino)-3-methyl-1-methoxybenzene or 4-n-octylamino-1-methoxybenzene.

14. A process according to claim 1, wherein the reactants of formulae (2) and (3) are 2-(4'-diethylamino-2'-hydroxybenzoyl)benzoic acid and 4-dibenzylamino-1-methoxybenzene.

15. A process according to claim 1, wherein the reactants of formulae (2) and (3) are 2-(4'-di-n-butylamino-2'-hydroxybenzoyl)benzoic acid and 4-phenylamino-3-methyl-1-methoxybenzene.

16. A process according to claim 1, wherein the reactants of formulae (2) and (3) are 2-(4'-diethylamino-2'-hydroxybenzoyl)benzoic acid and 4-tert.butylphenol.

17. A process according to claim 1, wherein the nonpolar organic solvent is toluene or xylene.

18. A process according to claim 1, wherein the addition step (2) of the reaction product is carried out at a temperature of 75° to 90° C.

19. A process according to claim 1, wherein the base is sodium hydroxide.

20. A process according to claim 1, which comprises condensing the ketonic acid of the formula (2) and the phenol derivative of formula (3) in a mixture of concentrated or fuming sulphuric acid at 10° to 40° C., adding the reaction product to an aqueous-organic medium containing toluene or xylene and a base and having a temperature of 70° to 85° C., and subsequently treating with a base at 70° to 85° C., and finally separating the toluene or xylene phase and isolating the fluoran of formula (1) by removing the solvent.

21. A process according to claim 15 wherein the compound of formula (1) melts at 180°–182° C.

* * * * *